US008695226B2

(12) United States Patent
Buettner

(10) Patent No.: US 8,695,226 B2
(45) Date of Patent: Apr. 15, 2014

(54) DEVICE FOR THREE DIMENSIONAL REPRESENTATION OF HORSEBACKS

(76) Inventor: Thomas Buettner, Dresden (DE)

( * ) Notice: Subject to any disclaimer, the term of this patent is extended or adjusted under 35 U.S.C. 154(b) by 230 days.

(21) Appl. No.: 13/352,293

(22) Filed: Jan. 17, 2012

(65) Prior Publication Data
US 2012/0180331 A1 Jul. 19, 2012

(30) Foreign Application Priority Data

Jan. 18, 2011 (DE) .......................... 10 2011 002 829
Sep. 2, 2011 (DE) .......................... 10 2011 053 233

(51) Int. Cl.
G01B 3/14 (2006.01)

(52) U.S. Cl.
USPC ................................. 33/511; 33/562

(58) Field of Classification Search
USPC ........... 33/511, 562, 451, 483, 464, 427, 474, 33/480, 481, 1 CC, 512, 514.2, 1 BB, 375, 33/551, 552; 54/44.1; 264/272
See application file for complete search history.

(56) References Cited

U.S. PATENT DOCUMENTS

| 1,093,867 | A | * | 4/1914 | LeGare | 33/340 |
| 2,162,602 | A | * | 6/1939 | Black | 33/375 |
| 2,743,528 | A | * | 5/1956 | Posthauer, Sr. | 33/375 |
| 2,746,164 | A | * | 5/1956 | Eitzen | 33/375 |
| 3,110,112 | A | * | 11/1963 | Dalgleish | 33/552 |
| 4,444,204 | A | * | 4/1984 | Bryant et al. | 600/594 |
| 4,593,476 | A | * | 6/1986 | Clark et al. | 33/529 |
| 6,769,234 | B2 | * | 8/2004 | Hadlock | 54/44.1 |
| 6,907,672 | B2 | * | 6/2005 | Said | 33/552 |
| 6,948,256 | B2 | * | 9/2005 | Ferrand | 33/511 |
| 7,805,854 | B2 | * | 10/2010 | Eaton | 33/551 |
| 8,425,434 | B2 | * | 4/2013 | Mulder | 600/587 |
| 2003/0221328 | A1 | | 12/2003 | Ferrand | |
| 2004/0112017 | A1 | | 6/2004 | Hadlock | |
| 2012/0017547 | A1 | * | 1/2012 | Rieser | 54/44.1 |

FOREIGN PATENT DOCUMENTS

| EP | 1214270 | 3/2001 |
| GB | 1587688 A | 4/1981 |
| WO | WO 97/17281 A1 | 5/1997 |
| WO | WO 2010/103108 A1 | 9/2010 |

* cited by examiner

Primary Examiner — Christopher Fulton
(74) Attorney, Agent, or Firm — Von Rohrscheidt Patents

(57) ABSTRACT

A device for three-dimensional representation of horsebacks through measurement points, comprising: plural vertically telescoping and column shaped segments which are connected with a frame and which include flexible transversal elements at their upper end which flexible transversal elements are bent like an umbrella and have flexible curvatures, wherein the vertical segments are configured to be variably offset from one another in the frame and configured fixable in a temporary manner and the curvature of the transversal elements that are bent in the shape of an umbrella is adjustable and fixable in a temporary manner, wherein the transversal elements include measuring points which are configured variably arrangeable in a vertical plane through devices for adjusting the curvature of the transversal elements, and wherein the measuring points of the transversal elements are arranged in the surface of the three-dimensional contour of the horseback.

8 Claims, 6 Drawing Sheets

FIG. 2

| H | A | B | C | D | E | | |
|---|---|---|---|---|---|---|---|
| L | 0 | HB | HC | HD | HE | | |
| 7 | A-B | B-0 | B-C | B-D | B-E | | |
| 14 | A1 | B1 | C1 | D1 | E1 | | |
| 21 | A2 | B2 | C2 | D2 | E2 | DF | BU |
| | A3 | B3 | C3 | D3 | E3 | | |

DEVICE FOR THREE DIMENSIONAL REPRESENTATION OF HORSEBACKS

RELATED APPLICATIONS

This application priority from German utility model application DE 10 2011 002 829.3 filed on Jan. 18, 2011, and German patent application DE 10 2011 053 233.1, filed on Sep. 2, 2011, both of which are incorporated in their entirety by this reference.

FIELD OF THE INVENTION

The invention relates to a device for three-dimensional true to scale representation of horsebacks.

BACKGROUND OF THE INVENTION

An anatomically correct representation of a horseback in three-dimensional space is required e.g. to fabricate horse saddles which are precisely adapted to the anatomy of the respective horse.

When a saddle is not specifically fabricated for a particular animal, there are problems during the use of the saddle that does not fit exactly, wherein the problems are caused by muscular tensions and interference with the motions of the horse. These problems are partially mitigated according to DE 600 12 949 T2 through a development of particular spacers for saddles that do not fit precisely, wherein imprint cushions for visualizing an imprint pattern of the pressure distribution of a saddle are being used.

When fabricating a new riding saddle, it is desirable to achieve the best possible precision and fit in order not to have to make additional efforts for adapting the saddle to the particular horse.

In the art, when fabricating a new saddle a horseback is measured with a tool that is similar to a fishbone. Thus plural parallel flexible metal rods are connected to a connecting element at a 90° angle. The tool is applied to the horseback, so that the connecting element contacts the horseback over the entire length of the connecting element. The protruding metal rods are then bent so that they adapt to the contour of the horseback through being applied to the contour of the horseback. Thus, the shape of the horseback can be replicated. When adapting the saddle, the fishbone shaped tool is used as a template from which an approximate replication of the horseback can be produced through cutting out pieces of cardboard or wooden plates.

A disadvantage of the prior art method is the independence of the measuring result from a position in space, this means the position of the connecting element relative to horizontal is not detected. When the fishbone shaped tool is applied to the horseback, it does not necessarily have to be horizontal. When the tool is subsequently held in ones hand, it can be tilted at will. The result that is represented in the tool therefore does not facilitate any conclusions with respect to the position of the saddle relative to horizontal and therefore an anatomically correct replication is virtually impossible.

BRIEF SUMMARY OF THE INVENTION

Thus, it is the object of the invention to provide a device through which horsebacks can be represented three-dimensionally with sufficient precision so that the result is reproducible any time.

The object is achieved through the features of the independent patent claims. Advantageous embodiments are defined through dependent patent claims.

The object of the invention is achieved in particular through a device for three-dimensional representation of horsebacks through measuring points, wherein the device includes plural vertically telescoping column-shaped segments which are connected to a frame. At an upper end of the segments, transversal elements are provided which are bent like an umbrella and whose curvature is flexible, wherein the vertical segments are configured so that they can be variably spaced from one another in the frame and fixated relative to one another in a temporary manner. The curvature of the transversal elements that are bent like an umbrella is also adjustable and fixable in a temporary manner. The transversal elements include measuring points which are variably arrangeable through devices for adjusting the curvature of the transversal elements in a vertical plane through adjusting the curvature of the transversal elements, wherein the measuring points on the transversal elements are arranged in the surface of the three-dimensional contour of the horseback.

The device is configured so that the devices for adjusting the curvature of the transversal elements and the measuring points arranged on the transversal elements are configured as telescoping struts, wherein the adjustment of the curvature of the transversal elements is provided through the telescoping struts which provides the fixation of the measuring points in the vertical plane in front view.

Alternatively thereto and particularly advantageously, the struts are adjustable in pairs in a horizontal position and through changing the angle relative to vertical with a sliding- and interlocking-mechanism so that the measuring points at the end of the struts which are also designated as offset points can be precisely positioned in the vertical plane.

It is a particular advantage of this alternative that the two struts of two associated offset points are connected with one another through the recited mechanism and are simultaneously adjustable through one operation. This is feasible in practical applications since typically the associated offset points are symmetrical to a center line.

Through a continuous adjustability of the height and of the angles of the two associated struts, the adjustment process can also be advantageously performed with electric stepper motors besides being performed by hand.

Another slightly more complex configuration in the struts is to make them telescoping and provide them connected on one side with the transversal element and on the other side with the column shaped element which makes each strut separately adjustable. This is favorable for the particular applications when the associated offset points are not symmetrical to the center line.

The device is advantageously configured with particularly fine adjustability in that the struts are connected with the transversal element directly at the measuring points.

In an advantageous embodiment, each of the measuring points besides the measuring point at the center of the horseback is associated with one strut, wherein the measuring points are adjustable in a particularly precise manner.

In practical applications, it has proven to be a particularly advantageous embodiment of the invention that six measuring points are arranged on the transversal element in addition to the measuring point in the center of the horseback, wherein the six measuring points are configured as measuring point pairs and the points of a pair are respectively arranged in a horizontal plane.

It has further proven to be advantageous that the device includes five vertical column-shaped telescoping segments, wherein each segment includes three measuring point pairs at the transversal element and the measuring point in the center of the horseback.

In order to capture measurement values at the horseback for adjusting the measurement points at the horseback imaging device, a dorsal ruler is provided. The dorsal ruler is a rigid profile with an end contact point A and a length measuring device for the horizontal position of the profile. Furthermore, height adjustment devices are provided in order to be able to adjust the horizontal position of the profile.

In an advantageous embodiment the dorsal ruler is characterized in that the position measuring device for the horizontal position of the profile is configured as a bubble level. A bubble level is a transparent hollow element filled with a liquid and a gas bubble for checking the horizontal or vertical position of the profile. The device for elevation adjustment is configured as an adjustable threaded rod. Alternatively thereto, the device for elevation adjustment is configured as a spacer rod or telescoping rod, wherein the key issue is to provide a quick and safe position adjustment of the dorsal ruler in a horizontal position.

The method for three-dimensional imaging of horsebacks through the device according to the invention for three-dimensional imaging of horsebacks and a dorsal ruler and flexible bending rulers includes the following steps: measuring the horseback and determining the measurement values for the measurement points of the three-dimensional contour of the horseback with the horizontally adjusted dorsal ruler and the flexible bending rulers and recording the measurement values, transferring the measurement values to the device for three-dimensional representation of horsebacks and adjusting the measurement points.

Measurement values are the distances of two points, whereas measurement points according to the invention are points in space which can be derived from the coordinates determined through the measurement values.

The device for replicating a horseback to be measured facilitates representing the contour of a horseback authentically true to scale and three-dimensionally correct. Thus the riding saddle which forms a link between a human anatomy and an anatomy of a horse can be configured in its position on the horseback according to the requirements of the particular horse.

Measuring the horseback which generates the values for using the device according to the invention, also designated as HBST (horseback simulation tool) is provided through a dorsal ruler which includes a rigid profile, preferably made from metal with an integrated bubble level and a height adjustable threaded rod for position adjustment of the dorsal ruler, wherein the elevation adjustable rod is arranged vertically.

When used according to the invention, the tool is applied in front on the highest dorsal process of the horseback and the threaded rod contacts the horseback in the back.

Through adjusting the threaded rod in vertical direction, the dorsal ruler is put in a precisely horizontal position through the bubble level. It is appreciated that the horizontal adjustment of the dorsal ruler can also be provided through a gyroscope or similar adjustment devices and telescoping elements for position adjustment instead of the threaded rod.

Characteristic points are marked on the center of the horseback. At these points, elevations from the horseback to the horizontal metal profile are being measured. Furthermore, the distances of these characteristic points from one another are being determined.

The contour of the horseback is replicated with flexible bending rulers vertically applied at the so-called intersection lines at these points. Based on the determined data which are recorded in a matrix in writing, the HBST can be adjusted now.

The HBST can be made e.g. from five stands which are movably attached to a frame and which are horizontally adjustable through a support. Each of these stands in turn includes a head element which is vertically adjustable in a telescoping manner. At the upper end of the head element there is a flexible spring steel band configured as a transversal element which can be adjusted through adjustable struts. All adjustable elements of the device are configured fixable at any selected position.

This way, the horseback can be replicated true to life and anatomically correct. The advantage is that a saddle that is to be adapted can be directly applied to the "replicated artificial horseback." The shape formed by the HBST can be used as a template by the saddle manufacturer, the saddle fitter or the horseback riding sports store and these businesses are thus enabled to produce or fit the saddle to the horse that has been measured or to select a fitting saddle from a number of finished saddles.

The invention has numerous advantages over the prior art. An unambiguous technical advantage is that angle errors can be excluded and adapting the saddle becomes much more precise. Since this device and the method of using the device minimize the probability of complex rework, this yields an economic advantage. The three-dimensional adjustability of the HBST facilitates representing various horsebacks quickly and without spending material. A saddle producer or saddle fitter or riding sports store is thus enabled to obtain a precise representation of the properties of a horseback also with data that has been generated far away and can produce or fit a saddle according to this data.

BRIEF DESCRIPTION OF THE DRAWINGS

Further details features and advantages of embodiments of the invention can be derived from the subsequent description of advantageous embodiments with reference to associated drawing figures, wherein:

FIG. 2 illustrates a matrix for recording the measurement results;

DETAILED DESCRIPTION OF THE INVENTION

Figure 1:
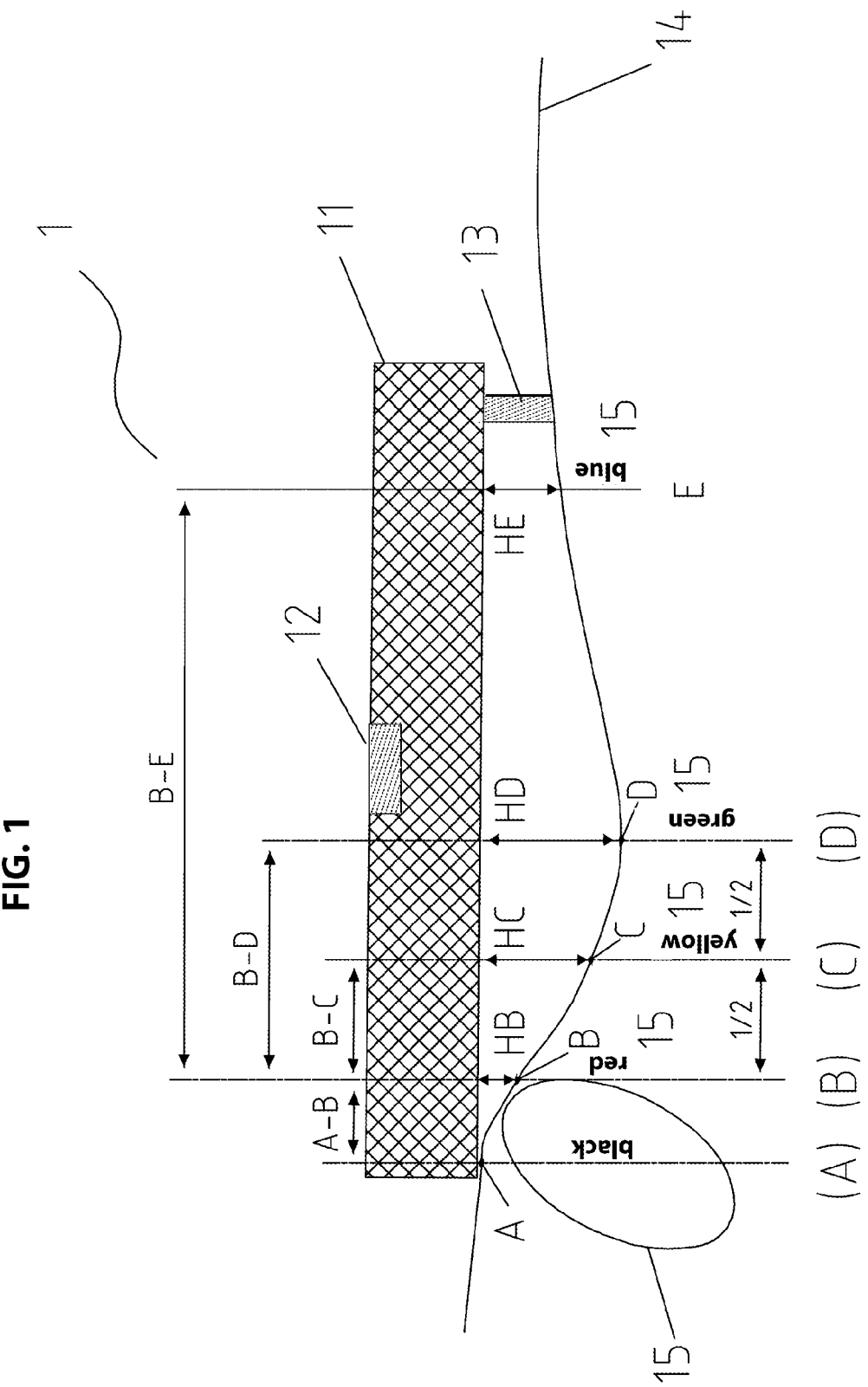
FIG. 1 illustrates a tool for capturing measurement points.

FIG. 1 illustrates the tool 1 applied to the horseback contour line 14 for generating measurement points, wherein the tool 1 is also designated as dorsal ruler which includes a rigid metal profile 11 with an integrated bubble level 12 and an adjustable threaded rod 13 arranged downward protruding for horizontal position adjustment. A designates the contact point of the tool 1 on the horse shoulder at the point of its strongest camber, B forms the baseline at the horse shoulder onset, C designates the trapeze line as a center between B and D, D designates the lowest point of the horseback and E marks the line downward from the $18^{th}$ vertebral body of the horseback. The bubble level 12 is used for precise horizontal alignment of the rigid metal profile 11 through the adjustable threaded rod 13.

FIG. 2 illustrates the matrix 2 for organized recording of the measurement values captured through the dorsal ruler, wherein the measurement values are used for adjusting the horseback simulation tool HBST.

Figure 3A:
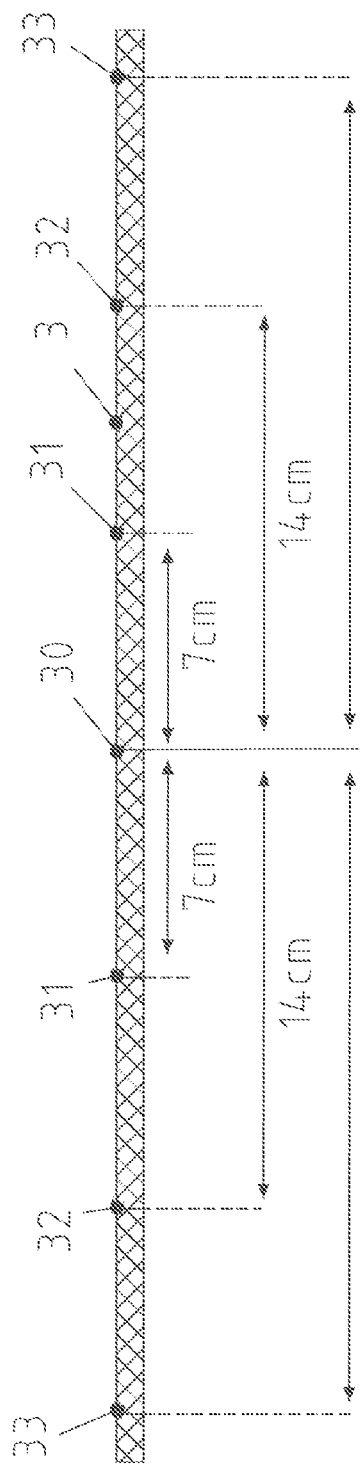
FIG. 3a illustrates a flexible bending ruler in top view.
Figure 3B:
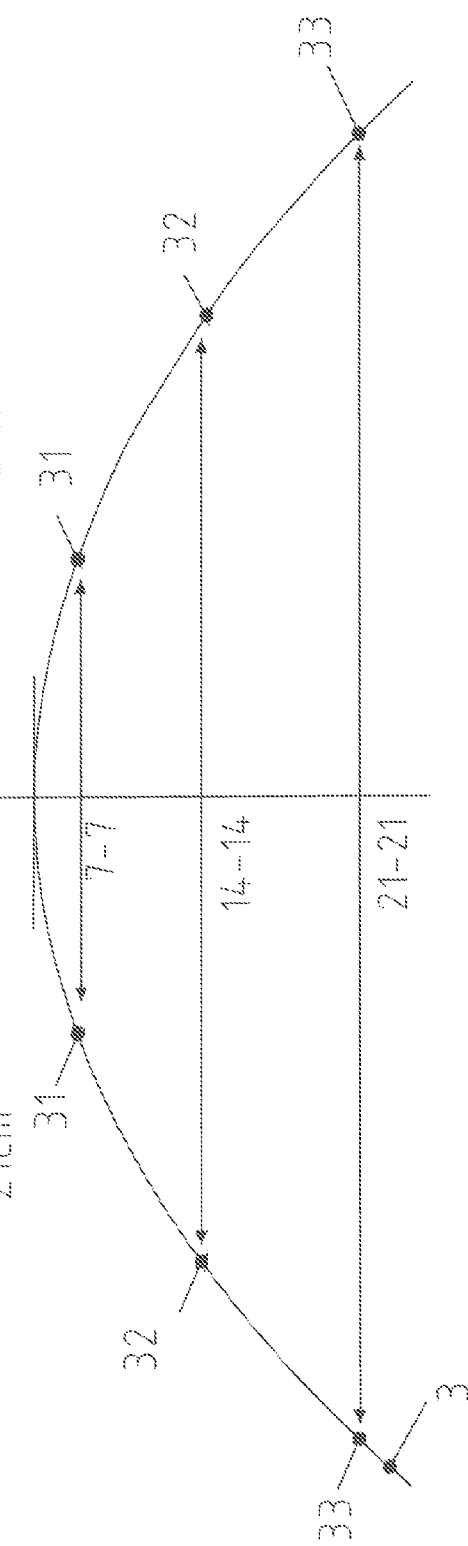
FIG. 3b illustrates a flexible bending ruler in a lateral view.

FIG. 3a illustrates a flexible bending ruler 3 in top view and FIG. 3b illustrates a flexible bending ruler 3 in lateral view. Measuring points are provided on both sides from the center of the horseback 30, wherein the measuring points are also designated as offset points, at 7 cm the measurement 7-7 designated with reference numeral 31 and at the offset points at 14 cm forming the measurement 14-14 with the reference numeral 32 and at the offset points at 21 cm with the reference numeral 33 forming the measurement 21-21.

Figure 4:
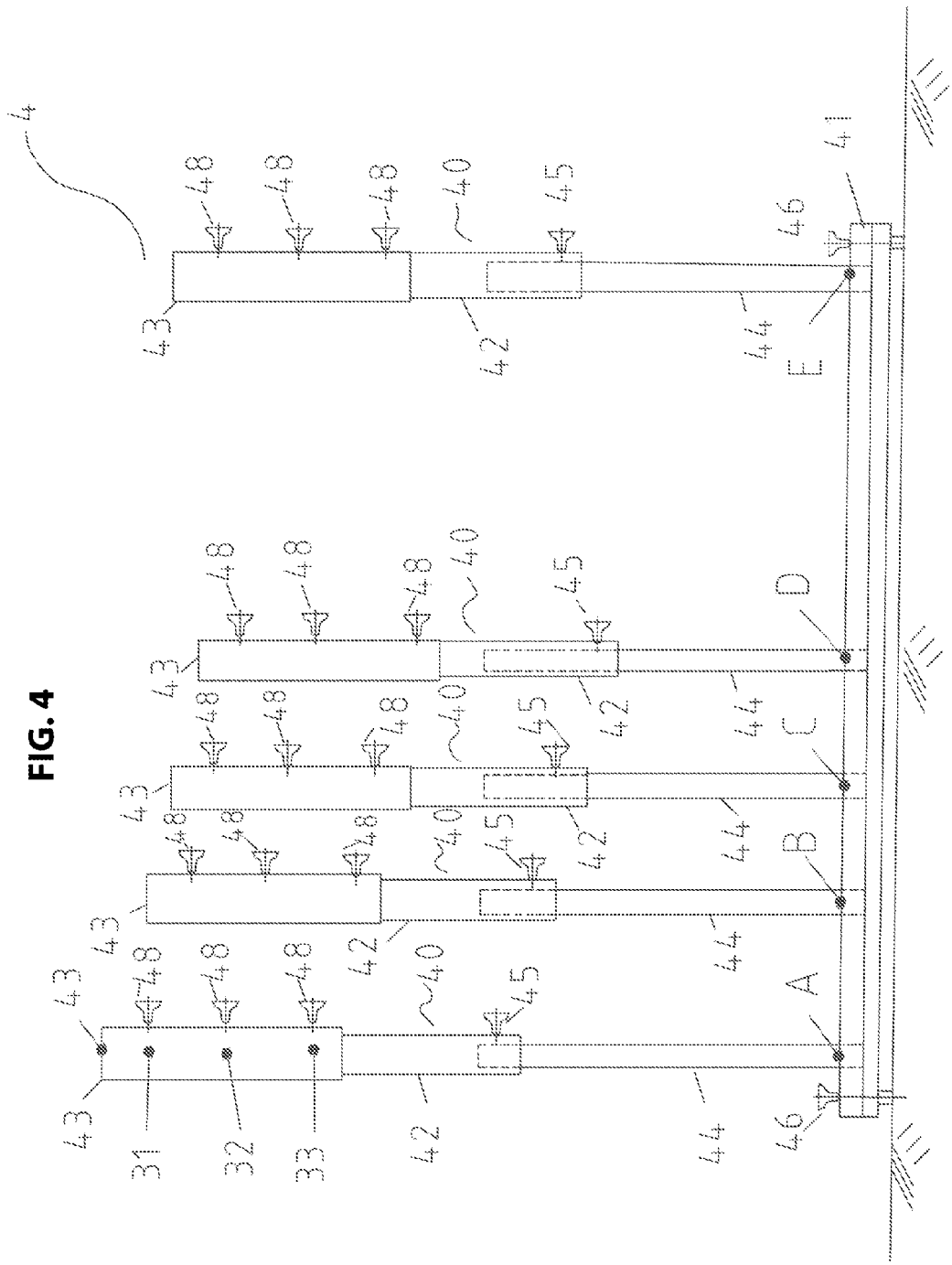
FIG. 4 illustrates a lateral view of the horseback representation device.

FIG. 4 illustrates the device 4 for representing a horseback HBST in a lateral view. The frame 41 with supports for movable segments 40 is provided with adjustment bolts 46 which facilitate adjusting a horizontal position of the frame 41. Plural segments 40 are movably arranged on the frame 41 and include a stand base 44 and a segment head portion 42 placed thereon in a manner so that it is vertically adjustable in a telescoping manner, wherein the segment head element 42 includes a transversal element configured as a spring steel band 43 at its upper end. The height adjustment of each segment head element 42 is fixated through fixation screws 45 or through a threaded spindle. Furthermore, the fixation bolts 48 are illustrated for the telescoping struts 47 which are not illustrated in this figure. In the side view, only one respective side of the transversal elements 43 with the measuring points 31, 32 and 33 and the measurement point 30 of the horseback center are illustrated in an exemplary manner at the left transversal element 43.

Figure 5:
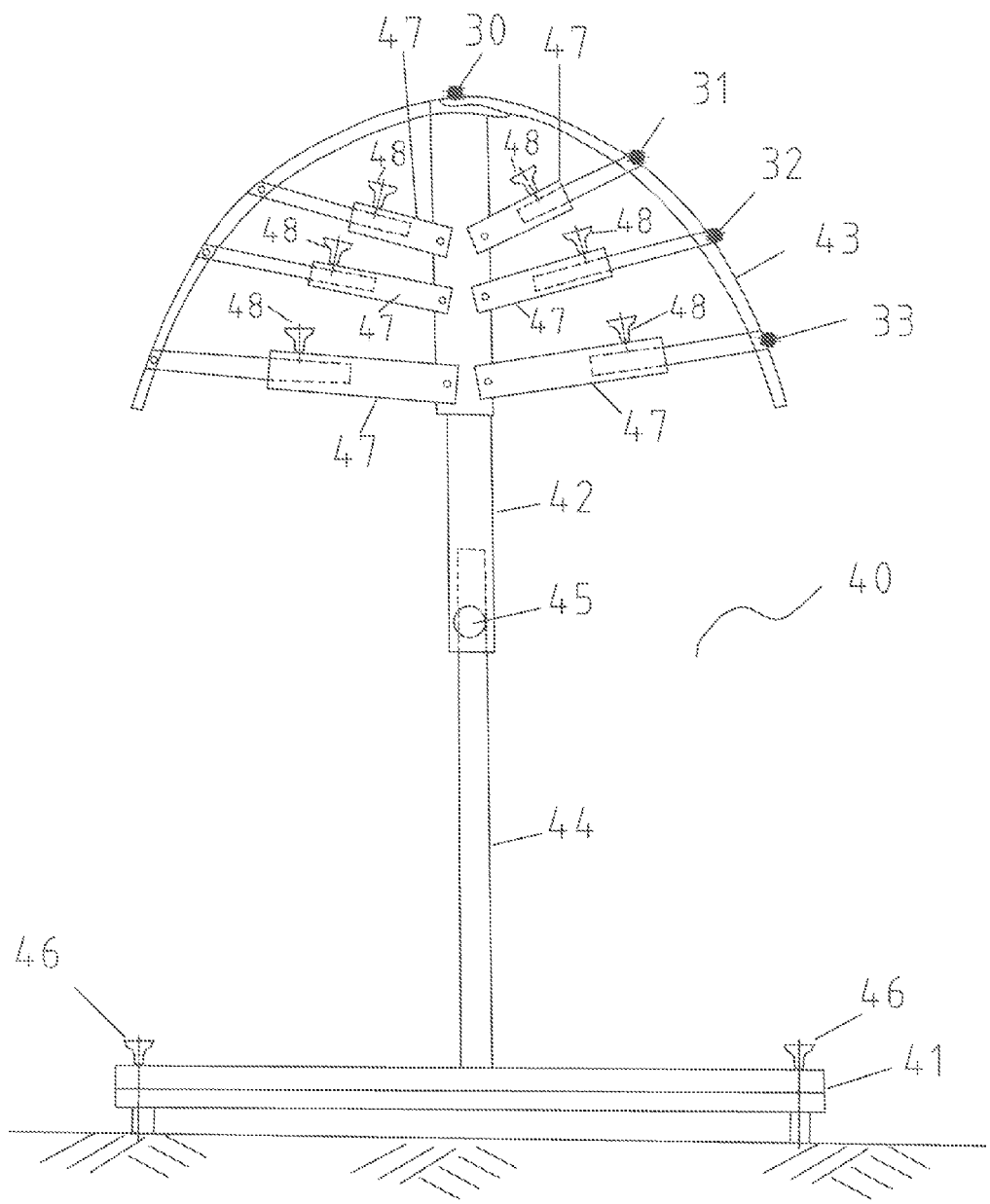
FIG. 5 illustrates a front view of the horseback representation device.

FIG. 5 illustrates the front view of the device for replicating a horseback clearly showing the configuration of the segment 40. The measurement points 30, 31, 32 and 33 are in a vertical plane illustrated in front view. The basic configuration of the device includes the frame 41 and the column shaped segment 40 and the transversal element 43 and is already described in the statements with respect to FIG. 4. The height adjustment segment head element 42 includes plural struts 47 that are individually adjustable and whose adjusted length determines the curvature and thus the shape of the spring steel band 43. Through the fixation screws 48 applied at the adjustable struts 47, the respective associated length of the strut 47 and thus the shape of the transversal element 43 configured as a spring steel element can be fixated.

Measurement points 30, 31, 32 and 33 are arranged on the transversal element 43, wherein the transversal elements 43 connect the measurement points with the segment head element 43 which provides a cross-section that is shaped with a contour like an umbrella.

Figure 6:
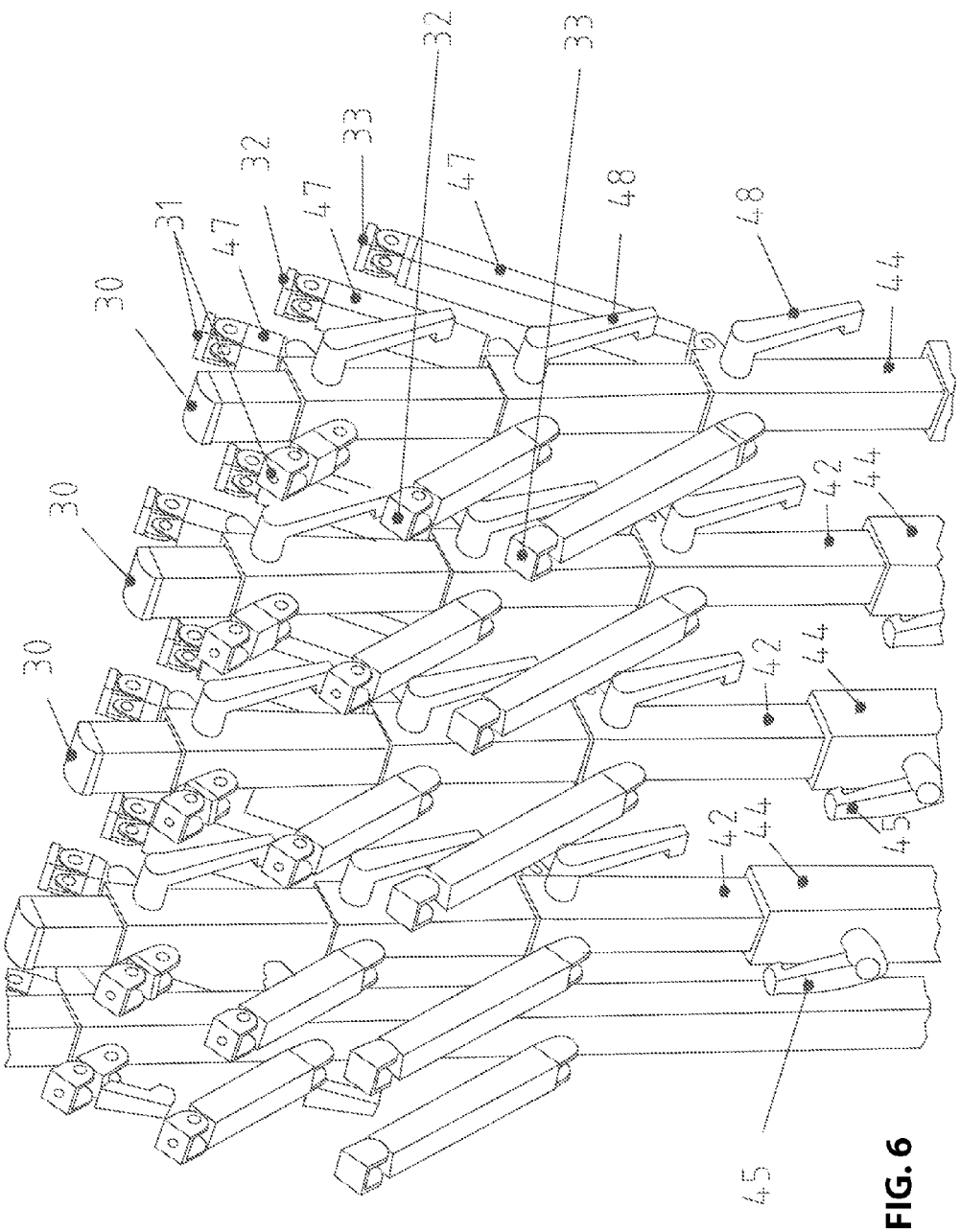
FIG. 6 illustrates segment head components with struts.

FIG. 6 illustrates a preferred embodiment of the segment head components 42 with the struts 47, wherein the segment head components are supported in the stand base 44 and configured to be positioned in elevation through the fixation devices 45. Differently from the configuration illustrated in FIG. 5, the struts 47 for two associated offset points are connected on an identical horizontal level through a sliding- and engagement mechanism, so that both struts 47 are continuously adjustable in vertical direction at the segment head element 42 with respect to their elevation and with respect to their angle relative to vertical. Thus, the struts 47 have a constant and non-telescoping length and the measurement points 31, 32 and 33 at the end of the struts 47 are placed through the entire movement of is the mechanism with the struts 47 in vertical direction and through the rotation of the struts 47 associated therewith they are placed at different angles. This is done with the presumption that the horseback that is being measured has a symmetrical contour with respect to the center line.

This embodiment is particularly advantageous in that only one adjustment movement at the fixation device 48 of the sliding- and engagement mechanism facilitates adjustment of both struts 47 with respect to their height and inclination so that a pair of measuring points 31, 32 and 33 can be positioned simultaneously in the vertical plane of the front view.

The translatoric movement of the struts 47 that are connected in pairs and their angular alignment that is dependent there from and the translatoric movement of the entire segment head element 42 facilitates using stepper motors for adjusting the measurement points 30, 31, 32 and 33. This facilitates an electrical and even fully automatic adjustment of the measurement points.

REFERENCE NUMERALS AND DESIGNATIONS

1 Dorsal ruler, tool for generating measurement values
11 Rigid profile
12 Position measuring device, bubble level
13 Elevation adjustment device, threaded rod, spacer rod, telescoping rod
14 Horseback contour line
A Contact point at strongest camber of horse shoulder
B Baseline at horse shoulder onset
C Trapeze line configured as a center between B and D
D Deepest point of horseback
E Line to first pectoral vertebral body of horseback
HB-HE Heights at the lines B through E
A-B Distance between A and B
B-C Distance between B and C
B-D Distance between B and D
B-E Distance between B and E
15 Color designation of the apex points of the intersection lines A through E
2 Matrix for capturing the measurement values
3 Flexible bending ruler
30 Measurement point horseback center
31 Measuring point, first offset point 7 cm from horseback center 30
32 Measurement point second offset point, 14 cm from horseback center 30
33 Measuring point third offset point 21 cm from horseback center 30
4 Device for representing a horseback (HBST)
40 Telescoping column shaped segment
41 Frame with support for the segments 40
42 Height adjustable segment head component
43 Transversal element of segment head component, spring steel band
44 Stand base
45 Fixation device for height adjustment of the segment head element 42, fixation bolt
46 Adjustment bolt for the frame 41
47 Devices for adjusting the curvature of the transversal elements, struts
48 Fixation device for struts 47, fixation bolt

What is claimed is:

1. A device for three-dimensional representation of horsebacks through measurement points, comprising:
   plural vertically telescoping and column shaped segments which are connected with a frame and which include flexible transversal elements at their upper ends which flexible transversal elements are bent like an umbrella and have flexible curvatures, wherein the vertically telescoping and column shaped segments are configured to be variably offset from one another in the frame and configured fixable in a temporary manner and the curvature of the transversal elements that are bent in the shape of an umbrella is adjustable and fixable in a temporary manner, wherein the transversal elements include measuring points which are configured variably arrangeable in a vertical plane through devices for adjusting the curvature of the transversal elements, and wherein the measuring points of the transversal elements are arranged in the surface of the three-dimensional contour of the horseback.

2. The device according to claim 1,
wherein the devices for adjusting the curvature of the transversal elements are configured as a sliding and/or engagement mechanism,
wherein two respective struts with equal length are connected with one another for representing the measurement point pair, so that the horizontal position also facilitates adjusting and fixating an inclination of the struts relative to vertical.

3. The device according to claim 1, wherein the devices for adjusting the camber of the transversal elements are configured as telescoping struts through which an adjustment of the camber of the transversal elements is respectively performed individually and thus the fixation of the measurement points is provided in the vertical plane.

4. The device according to claim 1, wherein the struts are connected on one side with the transversal element and on another side with the segment head element or the sliding- and engagement mechanism.

5. The device according to claim 1, wherein the struts are connected at the measurement points with the transversal elements.

6. The device according to claim 1, wherein each of the measuring points is associated with a strut.

7. The device according to claim 1, wherein six measuring points are arranged adjacent to the measurement point of the horseback center on a transversal element.

8. The device according to claim 1, wherein the device includes at least five segments.

* * * * *